United States Patent [19]

Firth

[11] 4,398,048
[45] Aug. 9, 1983

[54] PREPARATION OF 2,4,6-TRIALKYLPHENOLS

[75] Inventor: Bruce E. Firth, Elk Grove, Ill.

[73] Assignee: UOP Inc., Des Plaines, Ill.

[21] Appl. No.: 313,899

[22] Filed: Oct. 21, 1981

[51] Int. Cl.$^3$ .................. C07C 37/14; C07C 37/48
[52] U.S. Cl. ................................ 568/781; 568/784; 568/789; 568/790; 568/794
[58] Field of Search ............... 568/781, 783, 784, 785, 568/790, 805, 794, 789; 252/463

[56] References Cited

U.S. PATENT DOCUMENTS

| | | | |
|---|---|---|---|
| 2,923,745 | 2/1960 | Buls et al. | 568/794 |
| 3,968,172 | 7/1976 | Ichikawa et al. | 568/794 |
| 3,979,464 | 9/1976 | Leach | 568/804 |
| 4,275,248 | 6/1981 | Firth | 568/794 |
| 4,275,249 | 6/1981 | Firth | 568/789 |
| 4,283,574 | 8/1981 | Leach | 568/804 |

*Primary Examiner*—Werren B. Lone
*Attorney, Agent, or Firm*—James R. Hoatson, Jr.; Eugene I. Snyder; William H. Page, II

[57] ABSTRACT

Substantially improved yields of 2,4,6-trialkylphenols result from alkylating a mixture of phenol and 2,6-dialkylphenol, the latter being a by-product of the alkylation reaction. This results flows from an unexpected synergistic effect accompanying transalkylation. The continuous method of making 2,4,6-trialkylphenol based on this property affords the highly desirable trialkylated phenols in high yield.

22 Claims, No Drawings

PREPARATION OF 2,4,6-TRIALKYLPHENOLS

BACKGROUND OF THE INVENTION

Alkylated phenols are widely employed as antioxidants in a broad spectrum of products, spanning the gamut from foods to fuel oils. Among such alkylated phenols it has been found that 2,4,6-trialkylphenols are especially effective antioxidants in fuel oils, and in particular 2,4,6-triisopropylphenol is an excellent stabilizer for a broad range of fuel oils, including gasoline.

The 2,4,6-trialkylphenols can be prepared by several methods which are variations on the theme of alkylating phenol with an olefin over a bed of solid catalyst, such as alumina or silica, at an appropriate temperature. However, such methods have the inherent limitation that yields of 2,4,6-trialkylphenol in excess of about 70% are difficult, if not impossible, to achieve. Yet it is an economic imperative, not merely an economic desirability, that yields be in excess of 70% because other products of the alkylation reaction are substantially less effective as antioxidants than the 2,4,6-trialkylphenol.

It might appear that one way to achieve the necessary high yield of the trialkylphenol is by separating the 2,6-dialkylphenol, which is the other major product of reaction, and further alkylating it in a separate reaction. However, it has been found that 2,6-dialkylphenols are extraordinarily difficult to alkylate. For example, 2,6-diisopropylphenol fails to undergo substantial alkylation under conditions where the 2,4,6-triisopropylphenol is formed from phenol and propylene. Stated concisely, a problem in achieving the necessary high yields of 2,4,6-triisopropylphenol by alkylating the 2,6-diisopropylphenol by-product is that the 2,6-product is relatively inert under reaction conditions.

This invention rests on a solution to the prior described problem. In particular, the solution is based on the discovery that 2,6-diisopropylphenol undergoes transalkylation with phenol under reaction conditions, leading to the desired 2,4,6-triisopropylphenol. What is most surprising is that alkylation of a mixture of 2,6-diisopropylphenol and phenol literally affords synergistic results. For example, under a particular set of reaction conditions phenol can be converted to a mixture of roughly equal amounts of 2,6-diisopropylphenol and 2,4,6-triisopropylphenol. Under the same set of conditions, 2,6-diisopropylphenol is inert. Yet, if a 50-50 mixture of phenol and 2,6-diisopropylphenol is alkylated under these conditions, one obtains 30% of 2,6-diisopropylphenol and 70% 2,4,6-triisopropylphenol, whereas one would expect to obtain 75% 2,6-diisopropylphenol and 25% 2,4,6-triisopropylphenol were the alkylation reactions independent. This is shown schematically below.

Experimental: 2 parts phenol→1 part 2,6-+1 part 2,4,6-

Experimental: 2 parts 2,6-→2 parts 2,6-

Calculated: 2 parts phenol+2 parts 2,6-→3 parts 2,6-(75%)+1 part 2,4,6-(25%)

Experimental: 2 parts phenol+2 parts 2,6-→3 parts 2,6-(30%)+7 parts 2,4,6-(70%)

The invention described herein is basically a method of preparing 2,4,6-trialkylphenol from a feedstock of phenol and 2,6-dialkylphenol, the latter being recycled from the product stream. It affords the completely unexpected result in that the 2,4,6-trialkylphenol is formed from such a feestock in substantially higher yields than from either of the components alone under the same reaction conditions. In addition to the method having the important advantage of leading to higher overall yield of the desired trialkylphenol, it has the further advantage that use of 2,6-dialkylphenol as a diluent for phenol in the feedstock moderates the exotherm of the alkylation reaction. Although this latter benefit is incidental to the invention, nonetheless it is important from an engineering aspect because a sometimes serious problem attending extensive alkylation of phenol is the development of a hot spot in the continuous reactor, thereby causing oligomerization of the olefin or, in extreme cases, a runaway reaction.

SUMMARY OF THE INVENTION

An object of this invention is to prepare 2,4,6-trialkylphenols in superior yields by alkylating phenol over a bed of solid catalyst. An embodiment is a process comprising alkylating a mixture of phenol and 2,6-dialkylphenol with an olefin over said catalyst under alkylation conditions. In a more specific embodiment, the catalyst is fluorided alumina or silica alumina. In a still more specific embodiment, the olefin is propylene.

DESCRIPTION OF THE INVENTION

The invention described herein is a method of making 2,4,6-trialkylphenols comprising reacting a mixture of 2,6-dialkylphenol containing phenol with an olefin over a bed of solid catalyst under alkylating conditions, separating the unreacted 2,6-dialkylphenol from the formed 2,4,6-trialkylphenol, and recovering each of said alkylated phenols.

When the invention is embodied in the continuous process, there results a method of making 2,4,6-trialkylphenol comprising: (a) reacting phenol with an olefin over a bed of solid catalyst under alkylating conditions; (b) recovering the formed 2,4,6-trialkylphenol and separating the formed 2,6-trialkylphenol therefrom; (c) mixing the separated 2,6-dialkylphenol with phenol; (d) reacting the mixture of dialkylphenol and phenol with the olefin over the bed of solid catalyst under alkylating conditions, and repeating steps (b) through (d).

The olefins which may be used in the practice of this invention are monosubstituted olefins and alpha,beta-disubstituted olefins containing up to about 10 carbon atoms. Examples of suitable olefins include ethylene, propylene, 1-butene, 2-butene, 1-pentene, 2-pentene, 3-methyl-1-butene, 1-hexene, 2-hexene, 3-hexene, 3-methyl-1-pentene, 4-methyl-1-pentene, 4-methyl-2-pentene, and the isomeric heptenes, octenes, nonenes, and decenes corresponding to the prior description of suitable olefins. Propylene is an especially desirable and preferred olefin.

The amount of olefin used is a function of the feedstock composition. From about 3 to about 7 moles of olefin are used per mole of phenol, and from about 1 to about 3 moles of olefin are used per mole of 2,6-dialkylphenol. In a preferred embodiment from about 4 to about 6 moles olefin are used per mole phenol and about 2 moles olefin are used per mole of dialkylphenol.

The catalysts employed in the method of this invention are solid alkylating catalysts. Illustrative of such catalysts are acidic catalysts such as solid sulfonic acids (e.g., sulfonated polystyrene and other sulfonated resins), supported phosphoric and haloboric acids, metal halides, including those of boron and aluminum, and inorganic oxides such as alumina, silica, and their combinations. Of the aluminas, the fluorided and chlorided aluminas are especially desirable, as described in U.S. Pat. Nos. 4,275,248 and 4,275,249. In particular, aluminas containing from about 0.3 to about 5 wt.% fluoride or chloride are preferred. Among the silica-alumina catalysts, a proportion from about 1:9 to about 9:1 is satisfactory, with the range 1:3 to about 3:1 being preferred, and the range 4:6 to about 6:4 being especially preferred.

The feedstock of 2,6-dialkylphenol and phenol generally contains at least about 0.5 mole proportion phenol relative to the 2,6-dialkylphenol, by which is meant that there is 0.5 mole phenol per mole 2,6-dialkylphenol. This lower limit is dictated by economic considerations rather than operational characteristics of our process, and it is to be understood that a lower mole proportion of phenol may be usable, although not necessarily with equivalent results. It is more usual that the feedstock contains at least about 1 mole proportion phenol. The upper limit of phenol is not critical, though in practice there is seldom used more than about 3 moles of phenol per mole of 2,6-dialkylphenol. Because this invention is most commonly employed in a continuous method of making 2,4,6-trialkylphenol, the exact proportions will be determined by the split in recycle mode, as described below, which depends totally on considerations extrinsic to this invention.

Alkylating conditions include a pressure from about 100 psig to about 300 psig. Alkylating temperatures are in the range from about 150° to about 275° C., with the interval between 200° and 250° C. being preferred.

After the feedstock is alkylated, the 2,6-dialkylphenol is separated from the 2,4,6-trialkylphenol by any suitable means, as by distillation. For example, when distillation is used, the 2,6-dialkylphenol is recovered as the lower boiling material which is thereafter recycled with phenol as a feestock for further alkylation. The 2,4,6-trialkylphenol is recovered either as bottoms in the distillation or as the higher boiling fraction.

As previously mentioned, a particularly important embodiment of this invention occurs in its application to the continuous production of 2,4,6-trialkylphenol. Using as an example a fixed bed reactor containing a solid catalyst of 1:1 silica-alumina, reaction is begun by using as a feedstock phenol with about 4 to 6 molar proportions propylene at an inlet temperature from about 200° to about 250° C. The feed is passed over the catalyst where alkylation occurs to give a mixture whose major components are 2,6-diisopropylphenol and 2,4,6-triisopropylphenol. Effluent, which is the product mixture, is then separated by distillation into a fraction rich in 2,6-diisopropylphenol and one rich in 2,4,6-triisopropylphenyl, the latter being recovered as the desired product.

The initial alkylation is run so that the product composition of the effluent is from about 50% to about 65% 2,4,6-triisopropylphenol, the remainder being mainly 2,6-diisopropylphenol. The recovered 2,6-diisopropylphenol is then mixed with phenol and used as a feedstock, conditions being chosen such that the entire reactor is run under steady state conditions. By recycle mode is meant the split in the product composition by distillation. Assuming completely efficient separation one has between about 35% and about 50% split in the recycle mode, that is, from about 35% to about 50% of the product will be the 2,6-diisopropylphenol which is recycled with phenol as the feedstock to the reactor.

The examples given below merely illustrate this invention and do not limit it in any way.

EXAMPLES 1-3

All alkylations were performed in a continuous reactor containing a fixed bed of 1% fluorided alumina as the alkylating catalyst, using propylene at 500 psig plant pressure, and at a liquid hourly space velocity of about 0.5. In examples 1, 2, and 3 the feedstock is phenol, a simulated recycled feed, and a dialkylate feed, resp.

Example 1 of the table shows the product distribution when the feedstock is phenol only. As the data show, the most desirable product, 2,4,6-triisopropylphenol, is formed in yields of about 40 and 50% at 225° and 250° C., resp.

Example 2 gives the results of a simulated recycle run. What is meant by "simulated recycle run" is that the feedstock used approximates that contemplated at steady state conditions by recovering triisopropylphenols from the product stream, mixing the separated diisopropylphenols (along with a small amount of isopropyphenol) with phenol, and using the mixture as the feedstock. In this particular run, the feedstock was 58% phenol, 1% isopropylphenol, 29%, 2,6-diisopropylphenol, 5% other diisopropylphenols, and 7% 2,4,6-triisopropylphenol.

As the second and third entries in the table for Example 2 show, at 225° C. the effluent contains about 36% 2,4,6-triisopropylphenol which, considering the feedstock contained only 58% phenol, represents a 62% yield—a substantial improvement over the 40% yield of Example 1. The last two entries for Example 2 in the table show that the product at 250° C. contains about the same amount of dialkylate as the feed, i.e. this is the equivalent of the result where all the phenol has been directly converted to trialkylate. The preferred 2,4,6-triisopropylphenol is here formed in yields of about 80%, (100% conversion of phenol to trialkylate, 80% trialkylate is 2,4,6-triisopropylphenol) as compared to 55% when the feed is solely phenol.

In Example 3 the feedstock consisted of 80% 2,6-diisopropylphenol, 8% other diisopropylphenols, and 12% 2,4,6-triisopropylphenol. As the data of the table show, at 225° C. less than 40% of the 2,6-diisopropylphenol is further alkylated, and at 250° C. about half is alkylated. These data show the resistance of the 2,6-dialkylphenols to further alkylation and serve to further contrast the surprisingly beneficial results of Example 2 where the feed is a phenol and 2,6-dialkylphenol mixture.

| | Production of 2,4,6-Triisopropylphenol by Continuous Alkylation | | | | | | |
|---|---|---|---|---|---|---|---|
| EXAMPLE | TEMP. (°C. AT INLET) | TIME ON STREAM (HR) | MONO-ALKYLATE | 2,6-DIALKYLATE | OTHER | 2,4,6-TRIALKYLATE | OTHER |
| 1 | 225 | 36 | 1 | 42 | 6 | 39 | 11 |
| | | 58 | 1 | 42 | 8 | 40 | 9 |
| | | 122 | 4 | 45 | 7 | 37 | 7 |

-continued

| Production of 2,4,6-Triisopropylphenol by Continuous Alkylation | | | | | | | |
|---|---|---|---|---|---|---|---|
| EXAMPLE | TEMP. (°C. AT INLET) | TIME ON STREAM (HR) | MONO-ALKYLATE | 2,6-DIALKYLATE | OTHER | 2,4,6-TRIALKYLATE | OTHER |
|  | 250 | 186 | — | 22 | 6 | 53 | 19 |
|  |  | 204 | — | 22 | 7 | 54 | 14 |
|  |  | 222 | — | 22 | 9 | 55 | 15 |
| 2 | 225 | 24 | 2 | 50 | 6 | 35 | 7 |
|  |  | 44 | 2 | 51 | 6 | 37 | 4 |
|  | 250 | 80 | — | 26 | 6 | 52 | 15 |
|  |  | 98 | Trace | 29 | 7 | 51 | 13 |
| 3 | 225 | 58 | — | 53 | 5 | 37 | 6 |
|  |  | 62 | — | 48 | 6 | 39 | 7 |
|  | 250 | 20 | — | 40 | 6 | 45 | 9 |
|  |  | 24 | — | 34 | 7 | 48 | 11 |

What is claimed is:

1. A method of making a 2,4,6-trialkylphenol comprising reacting a feed mixture of a 2,6-dialkylphenol and phenol with an olefin over a bed of solid catalyst selected from the group consisting of alumina, fluorided alumina, chlorided alumina, and silica-alumina under alkylating conditions, separating the unreacted 2,6-dialkylphenol from the formed 2,4,6-trialkylphenol, and recovering each of said alkylated phenols.

2. The method of claim 1 where the olefin is propylene.

3. The method of claim 1 where the fluorided or chlorided alumina contains from about 0.3 to about 5 wt.% halide.

4. The method of claim 1 where the silica-alumina contains from about 1:3 to about 3:1 silica-alumina.

5. The method of claim 4 where the ratio is from about 4:6 to about 6:4.

6. The method of claim 1 where the alkylating conditions include a temperature from about 150° to about 275° C.

7. The method of claim 6 where the temperature is from about 200° to about 250° C.

8. The method of claim 1 where the mixture contains at least 0.5 mole proportion phenol.

9. The mixture of claim 1 where the mixture contains at least 0.5 mole proportion phenol.

10. A method of making a 2,4,6-trialkylphenol comprising:
   (a) reacting phenol with an olefin over a bed of solid catalyst selected from the group consisting of alumina, fluorided alumina, chlorided alumina, and silica-alumina under alkylating conditions;
   (b) recovering the formed 2,4,6-trialkylphenol and separating 2,6-dialkylphenol therefrom;
   (c) mixing the separated 2,6-dialkylphenol with phenol;
   (d) reacting the mixture from step (c) with the olefin over the bed of solid catalyst under alkylating conditions;
   and repeating steps (b) through (d).

11. The method of claim 10 where the olefin is propylene.

12. The method of claim 10 where the fluorided or chlorided alumina contains from about 0.3 to about 5 wt.% halide.

13. The method of claim 10 where the silica-alumina contains from about 1:9 to about 9:1 silica-alumina.

14. The method of claim 13 where the ratio is from about 1:3 to about 3:1.

15. The method of claim 14 where the ratio is from about 4:6 to about 6:4.

16. The method of claim 10 where the alkylating conditions include a temperature from about 150° to about 275° C.

17. The method of claim 16 where the temperature is from about 200° to about 250° C.

18. The method of claim 10 where the mixture of step (c) contains at least 0.5 mole proportion phenol.

19. A method of making 2,4,6-triisopropylphenol which comprises reacting a feed mixture of 2,6-diisopropylphenol and phenol with propylene over a bed of solid catalyst selected from the group consisting of alumina, fluorided alumina, chlorided alumina, and silica-alumina under alkylating conditions, separating 2,6-diisopropylphenol from the formed 2,4,6-triisopropylphenol, and recovering each of said phenols.

20. The method of claim 19 wherein said separated 2,6-diisopropylphenol is recycled to said feed mixture.

21. The method of claim 19 wherein said catalyst is fluorided alumina.

22. The method of claim 19 where the alkylating conditions include a temperature from about 150° to about 275° C.

* * * * *